United States Patent
Go et al.

(10) Patent No.: US 10,934,512 B2
(45) Date of Patent: Mar. 2, 2021

(54) MICROFLUIDIC PERFUSION CELL CULTURE SYSTEM

(71) Applicant: PUSAN NATIONAL UNIVERSITY INDUSTRY-UNIVERSITY COOPERRATION FOUNDATION, Busan (KR)

(72) Inventors: Jeung Sang Go, Busan (KR); Hyeong Jin Jeon, Busan (KR); Moon Jeong Kim, Busan (KR); Dong Hyeok Park, Yangsan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 356 days.

(21) Appl. No.: 15/774,501

(22) PCT Filed: Nov. 25, 2016

(86) PCT No.: PCT/KR2016/013732
§ 371 (c)(1),
(2) Date: May 8, 2018

(87) PCT Pub. No.: WO2017/091043
PCT Pub. Date: Jun. 1, 2017

(65) Prior Publication Data
US 2020/0239821 A1    Jul. 30, 2020

(30) Foreign Application Priority Data

Nov. 26, 2015  (KR) .................. 10-2015-0166102
Nov. 25, 2016  (KR) .................. 10-2016-0158138

(51) Int. Cl.
*C12M 3/06*     (2006.01)
*B01L 3/00*     (2006.01)
(Continued)

(52) U.S. Cl.
CPC ....... *C12M 23/16* (2013.01); *B01L 3/502715* (2013.01); *C12M 23/12* (2013.01);
(Continued)

(58) Field of Classification Search
None
See application file for complete search history.

(56) References Cited

U.S. PATENT DOCUMENTS

2004/0238052 A1* 12/2004 Karp .................. B01F 15/0205
                                                         137/822
2006/0008382 A1*  1/2006 Salamitou ......... B01L 3/502715
                                                         422/400
(Continued)

FOREIGN PATENT DOCUMENTS

KR    1020070011068    1/2007
KR    1020120040697    4/2012
(Continued)

OTHER PUBLICATIONS

International Search Report and Written Opinion issued in International Patent Application No. PCT/KR2016/013732, dated Jan. 13, 2017.
(Continued)

*Primary Examiner* — Holly Kipouros
(74) *Attorney, Agent, or Firm* — Norton Rose Fulbright US LLP

(57) ABSTRACT

A micro-fluidic system for a perfusion cell culture is disclosed. The system includes: a substrate; a micro-fluid injection channel defined in the substrate to guide fluid in a plane direction of the substrate; at least two micro-fluid branch channels defined in the substrate, wherein the branch channels are branched from the micro-fluid injection channel; micro-fluid outlet channels defined in the substrate, wherein each of the outlet channels extends from a distal end
(Continued)

of each branch channel to a top face of the substrate, wherein each outlet channel has each through-hole defined in the top face portion of the substrate; and well plates disposed on the top face of the substrate, wherein each of the well plates fluid-communicates with each outlet channel. The microfluidic system refers to a technique that adjusts a flow of liquid or gas of a very small amount (nanoliter or picoliter) in an extremely miniaturized device.

11 Claims, 11 Drawing Sheets

(51) Int. Cl.
    *C12M 1/00* (2006.01)
    *C12M 1/32* (2006.01)
    *C12M 1/02* (2006.01)
(52) U.S. Cl.
    CPC ............ *C12M 27/00* (2013.01); *C12M 29/10* (2013.01); *B01L 2300/06* (2013.01); *B01L 2300/0829* (2013.01)

(56) References Cited

U.S. PATENT DOCUMENTS

| | | | | |
|---|---|---|---|---|
| 2010/0029000 | A1* | 2/2010 | Zhong | C12M 23/12 435/383 |
| 2013/0320999 | A1* | 12/2013 | Deane | B01L 3/502776 324/649 |
| 2014/0134002 | A1* | 5/2014 | Brettschneider | F04B 41/06 417/53 |
| 2014/0322099 | A1* | 10/2014 | Zhou | B01L 3/5025 422/502 |
| 2015/0247112 | A1* | 9/2015 | Orr | C12M 23/12 506/9 |
| 2015/0323440 | A1* | 11/2015 | Okkels | G01N 11/08 73/861 |

FOREIGN PATENT DOCUMENTS

| | | |
|---|---|---|
| KR | 10-1412155 | 6/2014 |
| KR | 10-1446526 | 10/2014 |
| KR | 1020150048958 | 5/2015 |
| KR | 1020150098089 | 8/2015 |

OTHER PUBLICATIONS

Tian et al., "Microfluidics-based optimization of neuroleukin-mediated regulation of articular chondrocyte proliferation," *Molecular Medicine Reports*, 13:67-74, (2016).

Ziolkowska et al., "Integrated Passive Bubble Trap for Long-Term Cell Culture Microfluidic Systems," *16th International Conference on Miniaturized Systems for Chemistry and Life Science*, pp. 938-940, (2012).

\* cited by examiner

[Fig. 1]
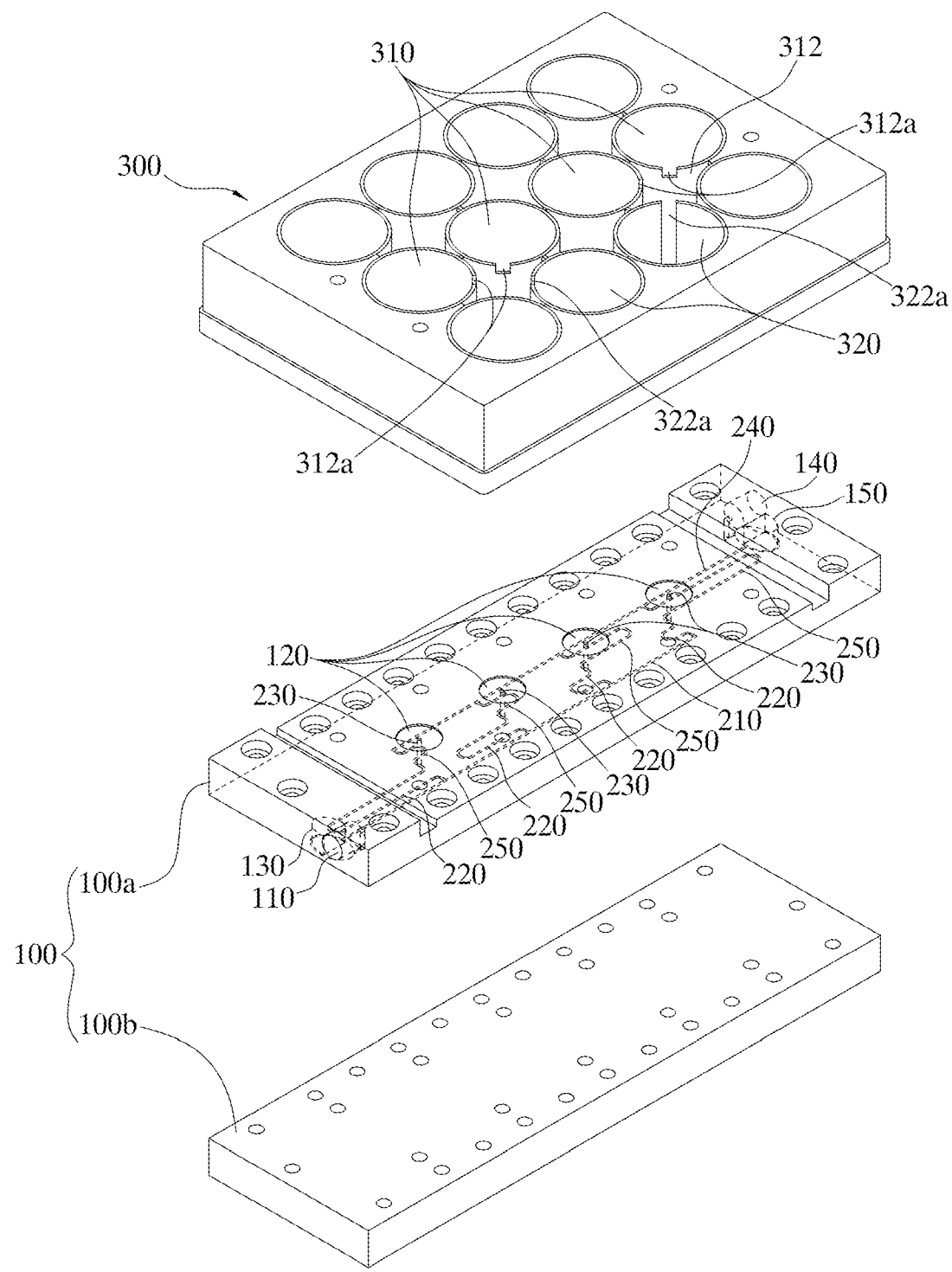

[Fig. 2]
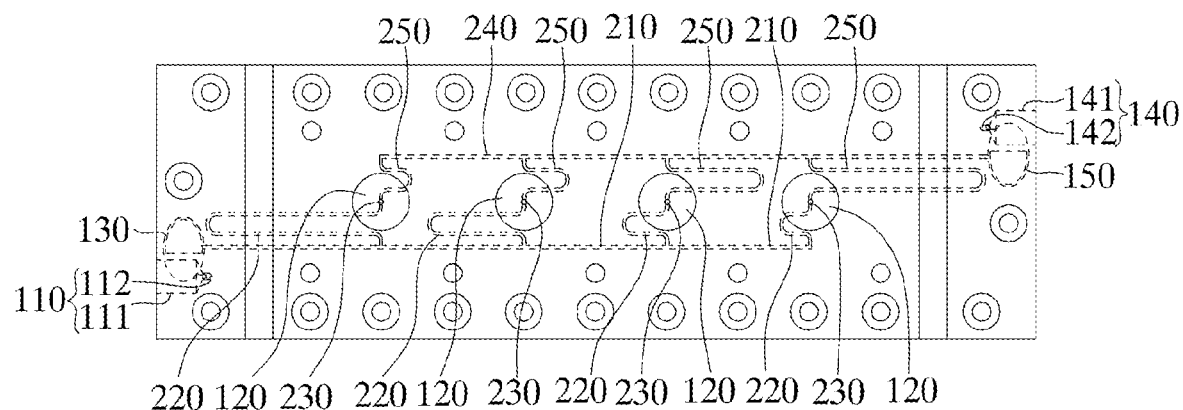
[Fig. 3]
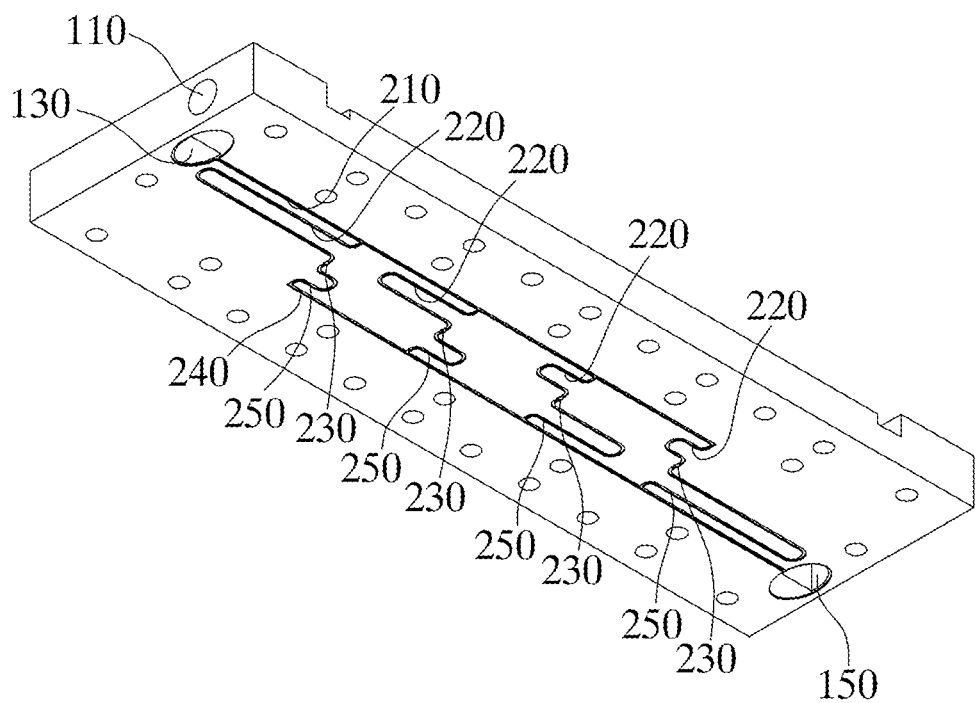

[Fig. 4]
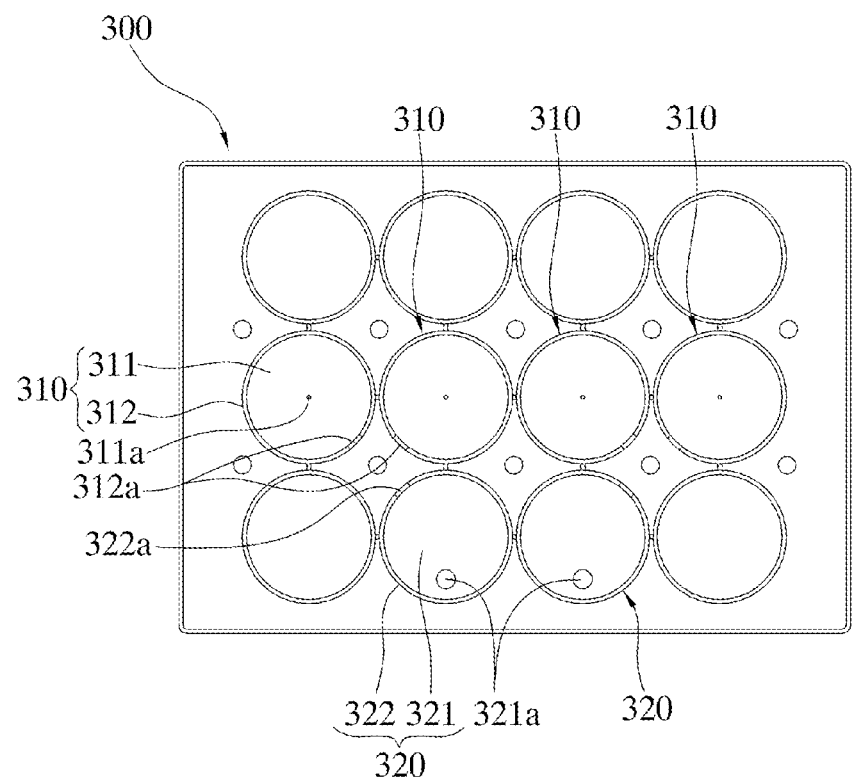
[Fig. 5]
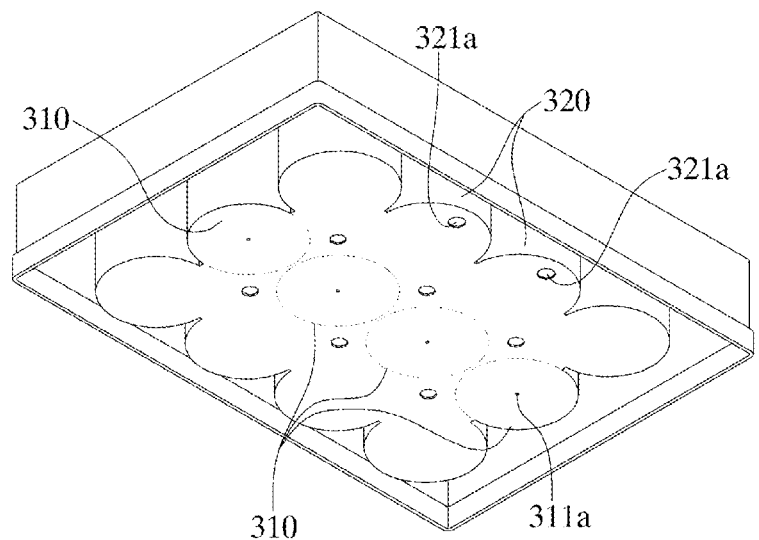

[Fig. 6]
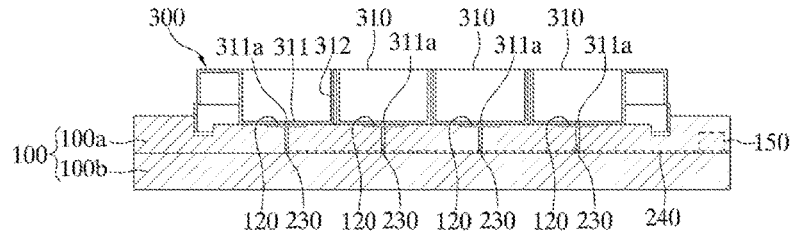
[Fig. 7]
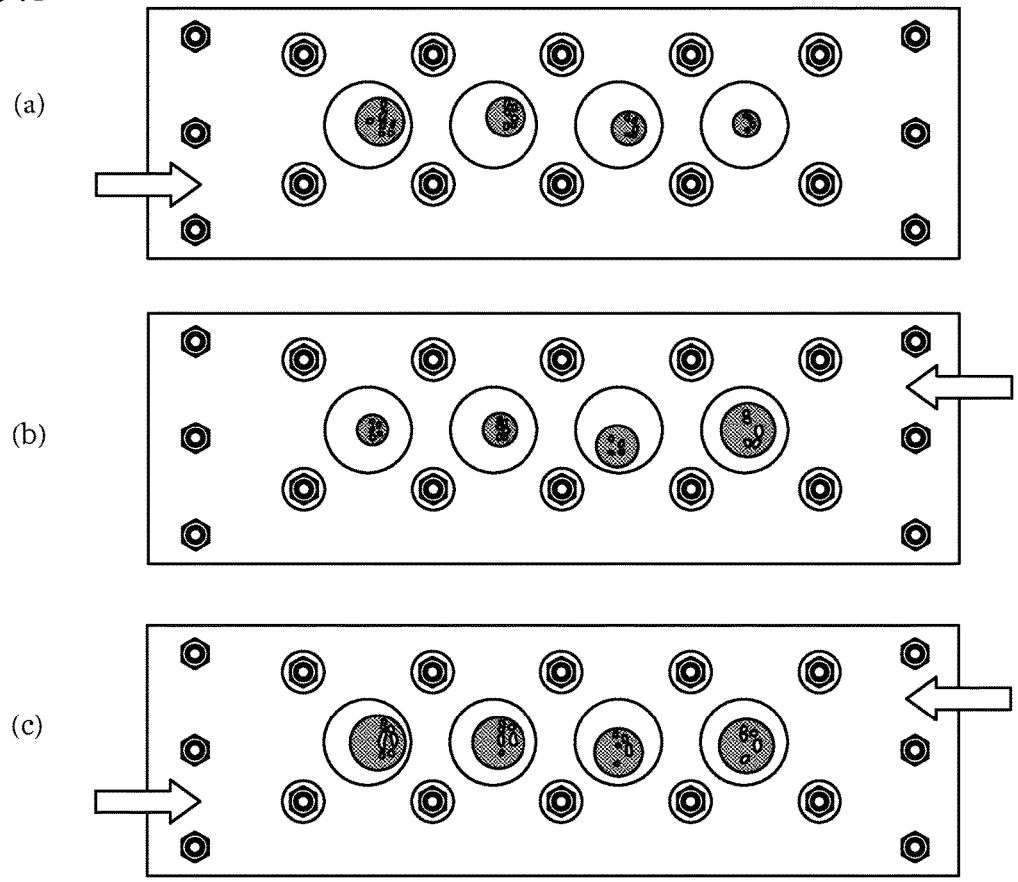
[Fig. 8a]
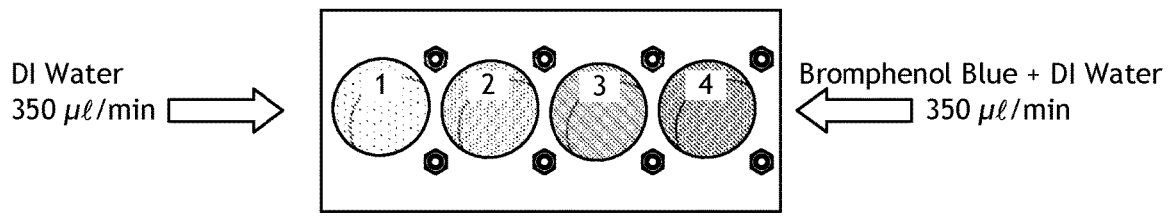

[Fig. 8b]
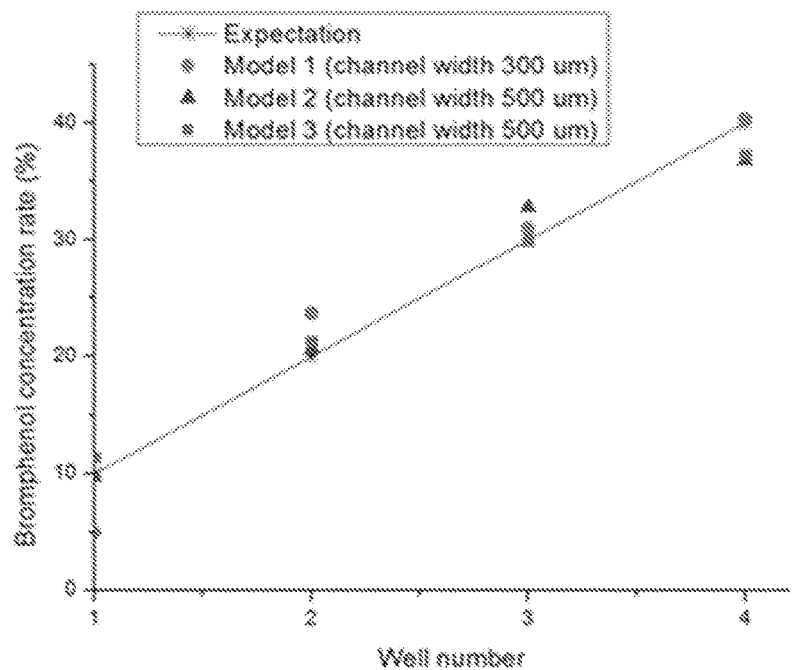
[Fig. 9a]
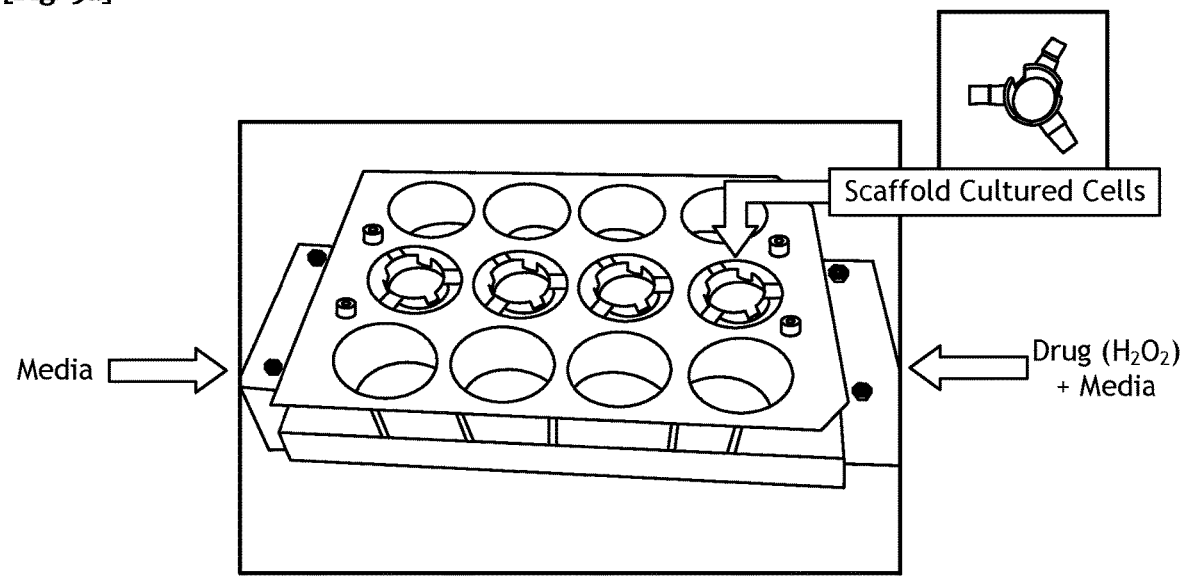

[Fig. 9b]
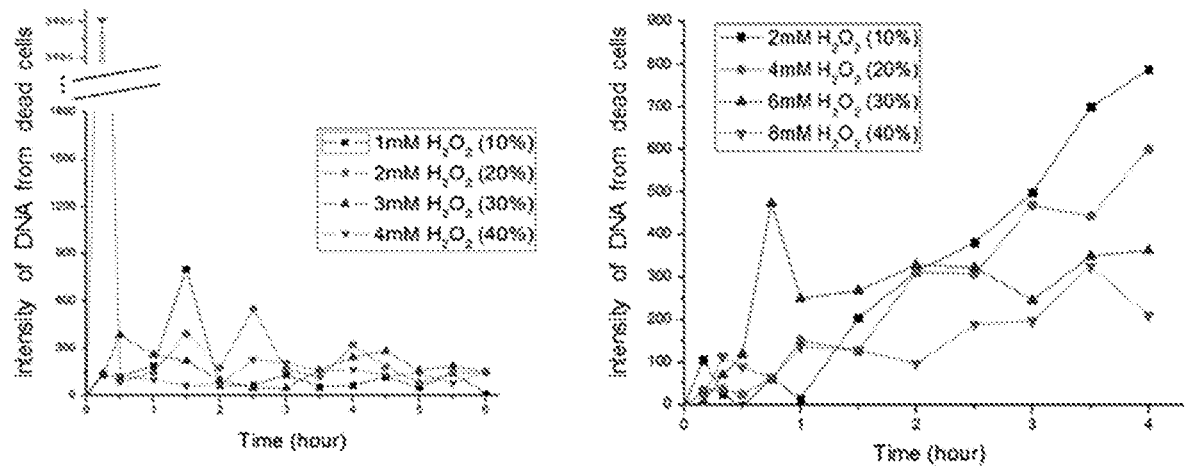
[Fig. 9c]
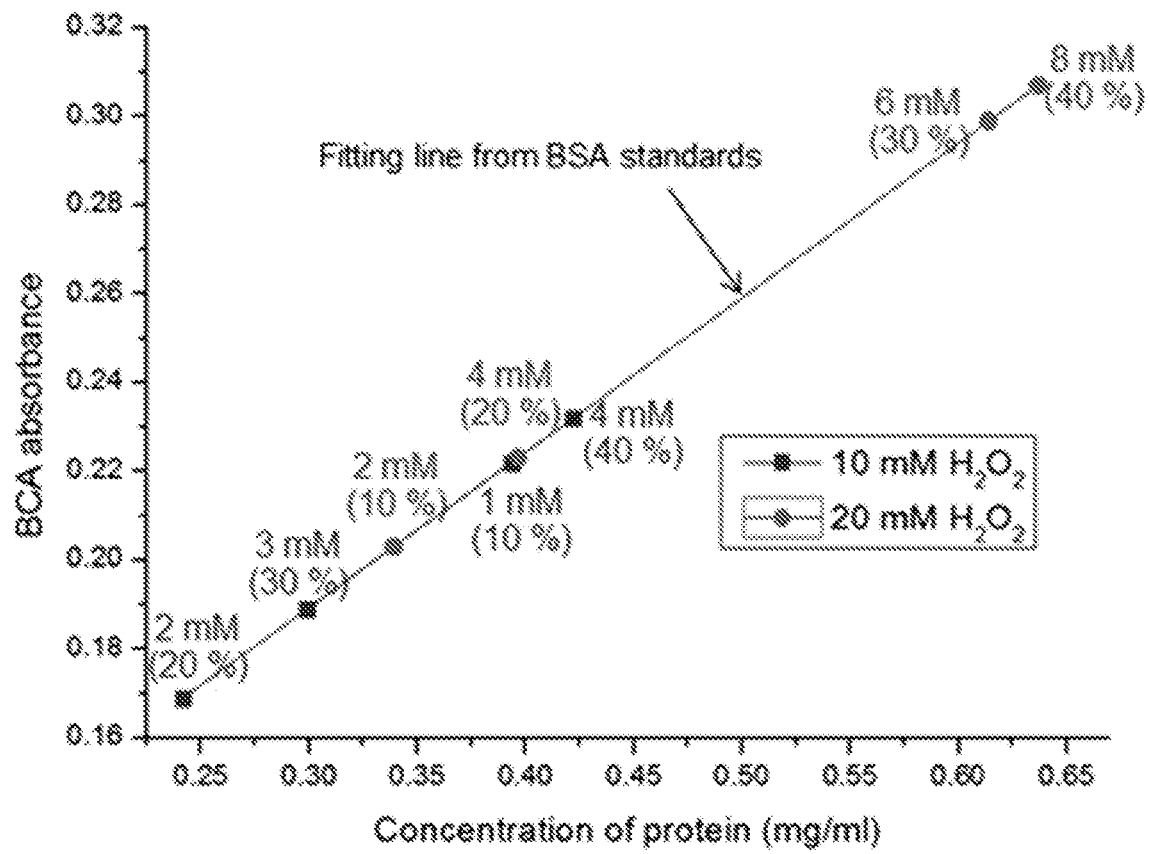

[Fig. 10]
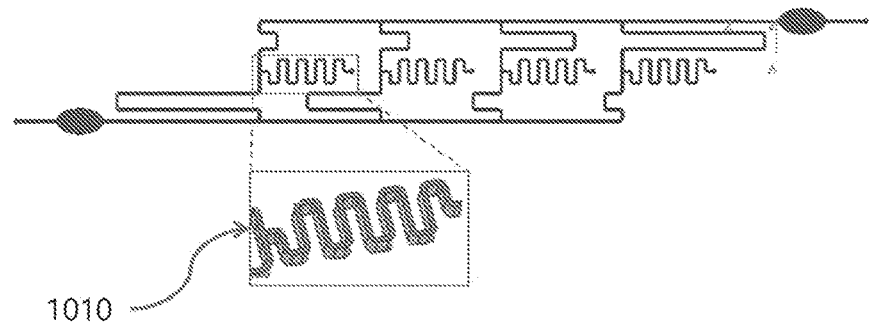
1010
[Fig. 11]
◆ Comparison in efficiency between mixing channels with 120 mm
* Straight mixer
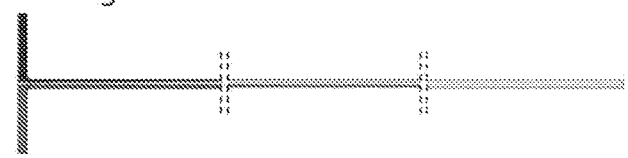
* Meander mixer
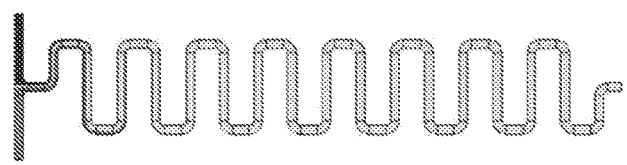
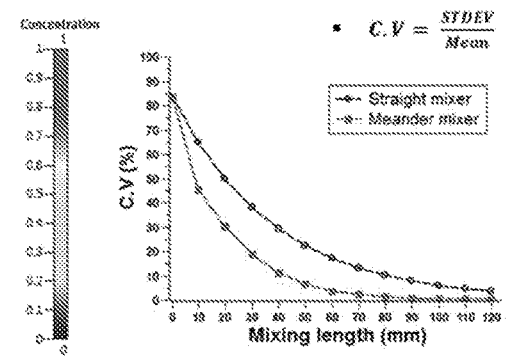
* $C.V = \frac{STDEV}{Mean}$
[Fig. 12]
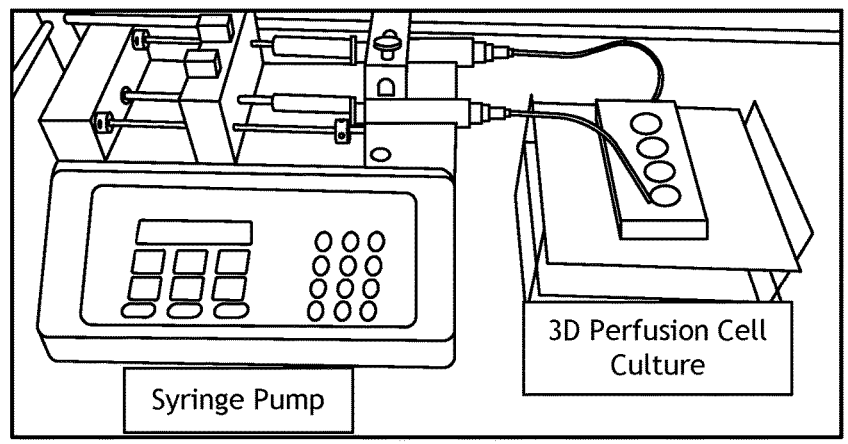

[Fig. 13]
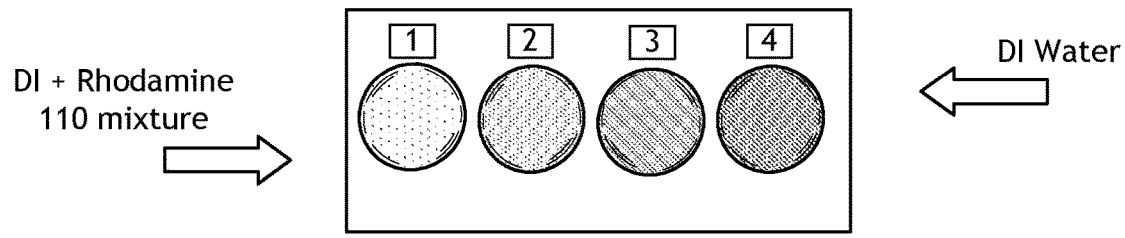
[Fig. 14]
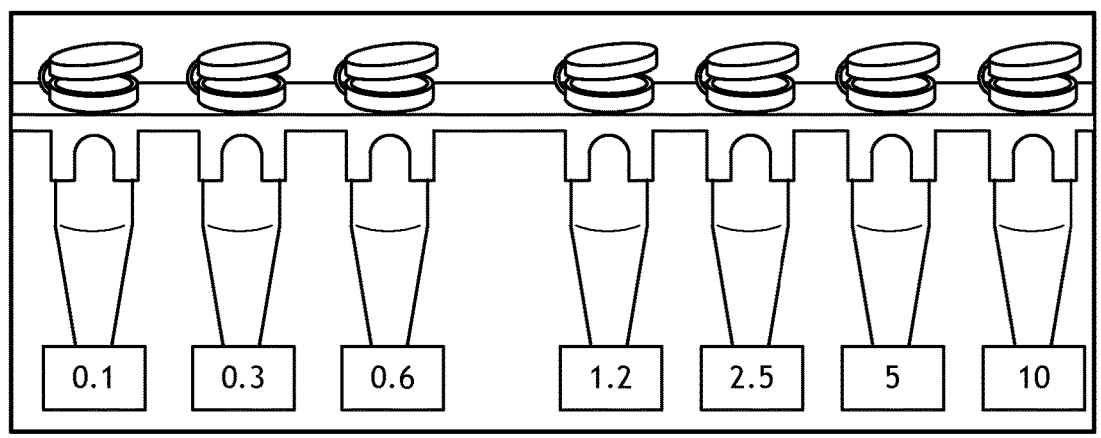
[Fig. 15]
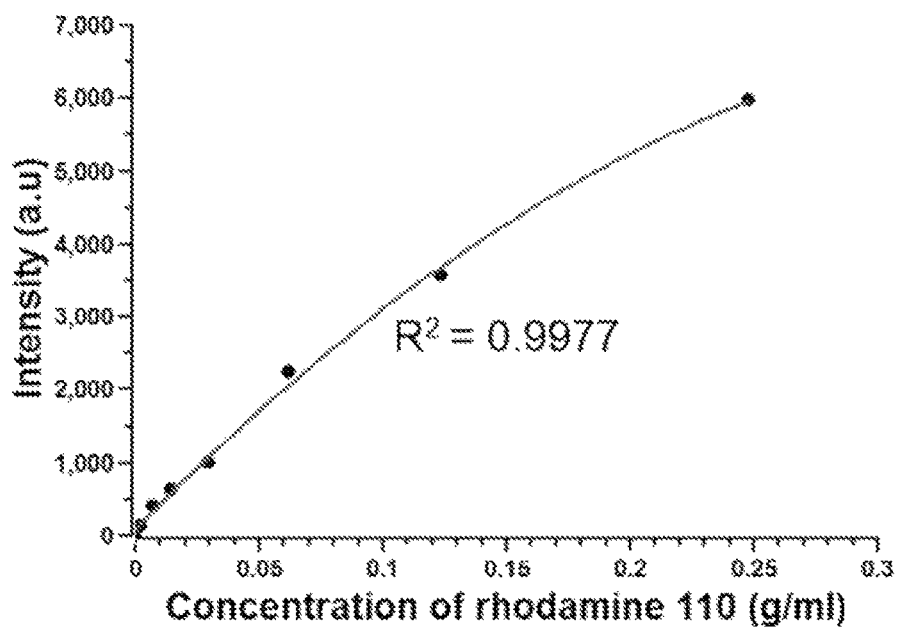

[Fig. 16]
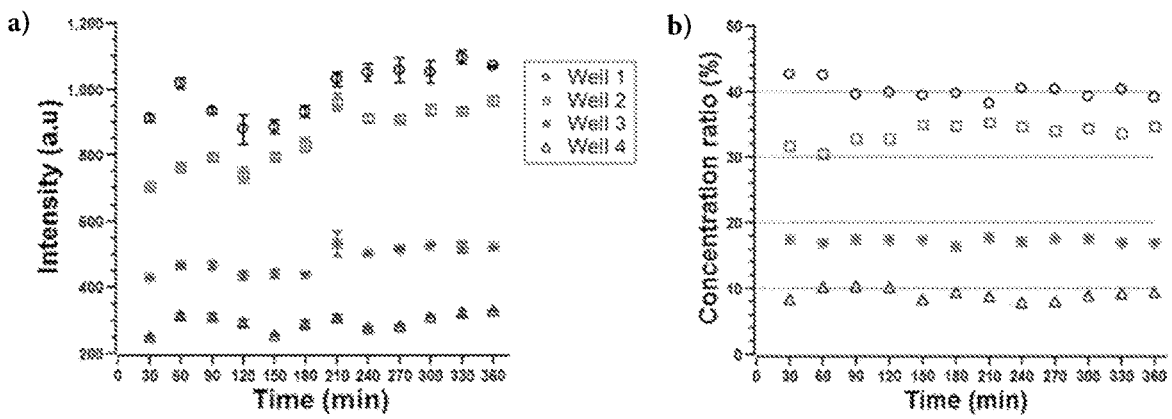
[Fig. 17]
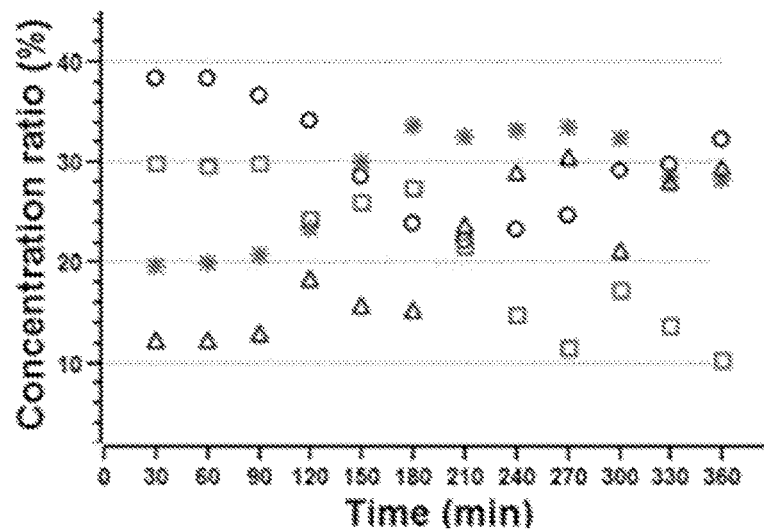
[Fig. 18]
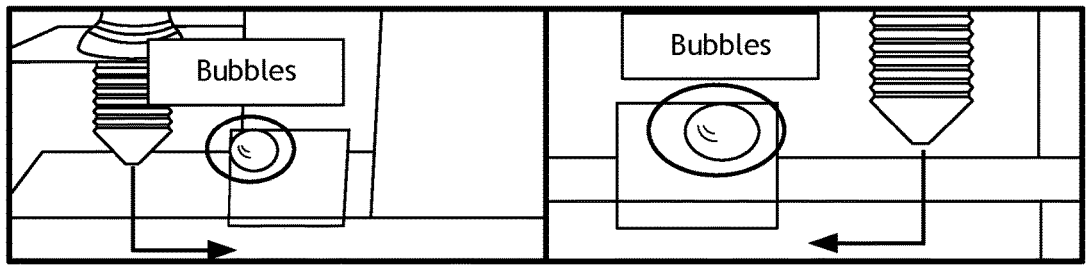

[Fig. 19]
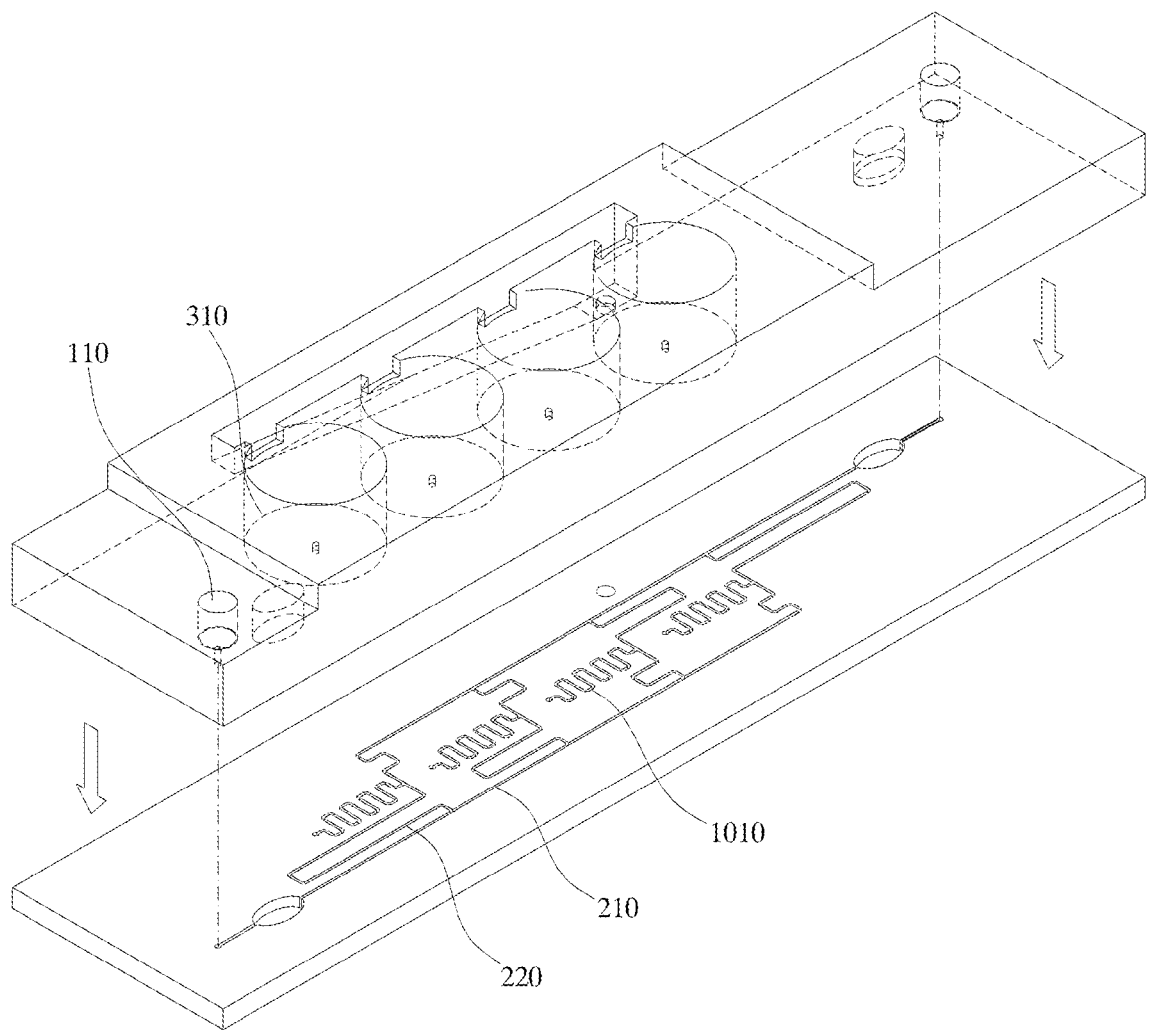

[Fig. 20]
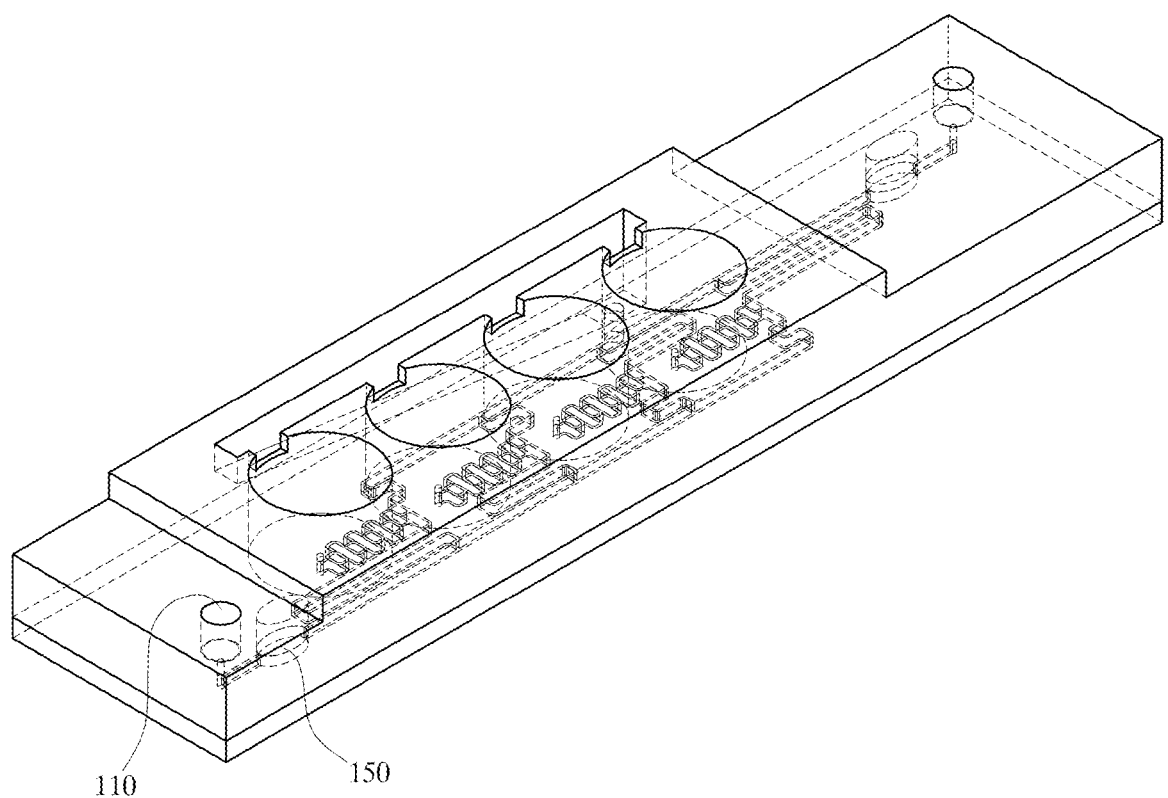

MICROFLUIDIC PERFUSION CELL CULTURE SYSTEM

TECHNICAL FIELD

The present disclosure relates to a system for a cell culture, more particularly, a micro-fluidic system for a perfusion cell culture to enable a 3D cell culture.

RELATED ART

A cell cultured by a conventional cell culture technique is a monolayer cell which is spread in a two-dimensional direction. Thus, the cell cannot construct a three-dimensional structure of a cell in a living body. Further, the cell cannot maintain a specific function of a cell in a living body for a long time. Therefore, there is a problem in that when the cell cultured by the conventional cell culture technique is used, an accuracy of the simulation is not ensured.

Meanwhile, in the conventional cell culture experiment, the cell is grown on a general plate while periodically changing a culture media therein, Thus, the conventional cell culture experiment is executed in a different environment from that in the living body. Alternatively, in a micro-fluidic system, a cell is grown in a flow of a culture media in a very small area in a micro unit. Since micro-fluidic channels included in the micro-fluidic system have very small sizes, the micro-fluidic system provides a physical environment similar to that of the living body and supplies a sufficient oxygen and facilitates a rapid diffusion of a nutrient at the same time. This provides a more suitable environment for the cell than an ordinary macro scale experiment for a cell-related experiment. Thus, a more accurate experimental result may be obtained. There have been many studies related to a cell chip for the micro fluidic system. Up to now, however, cell experiments have been predefined using a 2D system having a coating, on surfaces of the micro-fluidic channels.

However, such a 2D experiment cannot obtain an accurate result because the living body has basically a 3D structure. The cell is sensitive to even a minute change in a surrounding environment. Thus, due to the change, a completely different experimental result may be shown. Therefore, studies for culturing the cell in a 3D environment are under way.

Therefore, when the micro-fluidic system is incorporated into the 3D cell culture technology, cell movement, interaction between the cells, and interaction between the cell and an extracellular matrix as observed in various phenomena in a human body such as an angiogenesis, an immune response, and a cancer metastasis may be directly observed and analyzed with a high resolution. Further, various physical and chemical stimuli may be applied to the cell. Thus, there is an advantage that how certain factors, environments, etc. or combinations thereof affects the cell may be studied systematically.

PRIOR ART DOCUMENT

Patent Literature (Patent Document 1) Korean Patent No. 10-1412155

SUMMARY

A purpose of the present disclosure is to provide a perfusion cell culture system in which an accurate concentration distribution and evaluation are possible and a microenvironment is accurately simulated.

The present disclosure relates to a perfusion cell culture system using a micro-fluidic channel system.

The present disclosure uses the micro-fluidic system. The micro fluidic system refers to a technique that adjusts a flow of liquid or gas of a very small amount (nanoliter or picoliter) in an extremely miniaturized device. Thus, unlike a macro system, the micro-fluidic system shows specific characteristics such as a streamline flow, a large surface area, and a larger surface tension than inertia. In accordance with the present disclosure, the micro-fluidic system may precisely distribute a nutrient to the cell culture system. Thus, the perfusion cell culture system may be accurately controlled and reliably evaluated.

A micro-fluidic system for a perfusion cell culture, the system comprising: a substrate; a micro-fluid injection channel defined in the substrate to guide fluid in a plane direction of the substrate; at least two micro-fluid branch channels defined in the substrate, wherein the branch channels are branched from the micro-fluid injection channel; micro-fluid outlet channels defined in the substrate, wherein each of the outlet channels extends from a distal end of each branch channel to a top face of the substrate, wherein each outlet channel has each through-hole defined in the top face portion of the substrate; and well plates disposed on the top face of the substrate, wherein each of the well plates fluid-communicates with each outlet channel.

The nutrient and/or oxygen necessary for the cell culture are provided into the well plate through the micro-fluid channels, and the cell is cultured in the well plate. The cultures in the well plates are discharged through discharging holes in the upper ends of the well plates respectively. Thus, a perfusion system may be provided in which the fluid is continuously supplied to the micro channels and then is continuously discharged through the discharging holes.

Lengths of the branch channels are different from each other so that the branch channels have different flow rates based on Poiseuille's law.

$$R = \frac{\Delta P}{Q} \Rightarrow L = \frac{\pi d^4 P}{128\mu} \qquad \text{[Equation 1]}$$

In this equation, R: resistance, P: pressure drop, Q: flow rate, diameter of channel, μ: viscosity coefficient, and L: length of channel.

Based on the Poiseuille's law, the fluids flow at the different flow rates depending on the different lengths of the micro channels. That is, the fluid flowing through the micro-fluid injection channel is divided and flowed into the micro-fluid branch channels. In this connection, divided flows into the micro-fluid branch channel have different flow rates due to the different lengths thereof.

The micro-fluid branch channels are sequentially arranged in a flow direction of the injected fluid from the injection channel, wherein the lengths of the branch channels are configured such that the flow rates increase or decrease gradually between the micro-fluid branch channels. The flow rates of each branch channel are set to linearly increase of decrease, which facilitates comparative evaluation of the supply nutrients of each well plate.

The substrate has an inlet channel defined therein for injecting micro-fluid to the injection channel, wherein the substrate has a bubble trap defined therein between the inlet channel and the injection channel. The bubble trap is, for example, a macro-sized space defined on a side of the micro channel, which is defined higher than the channel. When gas (bubble) is contained in the fluid injected from the inlet channel to the micro-fluid injection channel, the bubble (gas) reaches the bubble trap and rises up and exits into the bubble trap, while the fluid moves into the micro-fluid injection channel.

The substrate has a plurality of cavities defined in a top face portion thereof, wherein each through-hole in the outlet channel communicates with each cavity, wherein each well plate has at least one bottom-hole, wherein a longest width of each cavity is smaller than a shortest width of a bottom face of each well plate, wherein a space is defined between a bottom face of each well plate and an inner face of each cavity, wherein fluid discharged from each through-hole is stored in each cavity, and, then, the fluid from the cavity is inflowed to each well plate through said at least one bottom-hole.

Each well plate has a lateral opening defined in an upper end of a side wall thereof, wherein a culture is discharged from each well plate through, the lateral opening.

The substrate further includes two or more further, micro-fluid branch channels branched from the further micro-fluid injection channel arranged at the other side of the well plate row where the injection channel is not arranged and the further micro-fluid branch, wherein a distal end of the branch channel joints with a distal end of said further branch channel, wherein each of said further branch channels fluid-communicates with each micro-fluid outlet channel.

Lengths of the further branch channels are different from each other so that the further branch channels have different flow rates based on Poiseuille's law.

The further micro-fluid branch channels are sequentially arranged in a flow direction of the injected fluid from the further injection channel, wherein the lengths of the further branch channels are configured such that the flow rates increase or decrease gradually between the further micro-fluid branch channels.

The substrate has a further inlet channel defined therein for injecting micro-fluid to the further injection channel, wherein the substrate has a further bubble trap defined therein between the further inlet channel and the further injection channel.

The substrate has mixing channels defined therein, wherein each mixing channel extends from each jointing point to each micro-fluid outlet channel, Each mixing channel includes a meandering section.

According to the present disclosure, the nutrient supply from the micro-fluidic system to the perfusion cell culture system may be controlled based on an accurate concentration distribution. The supply may be observed for comparison and analysis. Thus, it is possible to observe and quantitatively evaluate a tumor growth depending on input of the various nutrients and oxygen concentration.

BRIEF DESCRIPTION OF THE DRAWINGS

FIG. 1 is an exploded, perspective view showing a structure of a micro-fluidic system for a perfusion cell culture in accordance with the present disclosure.

FIG. 2 is a plan view of an upper plate of a substrate shown in FIG. 1.

FIG. 3 is a bottom perspective view of an upper plate of a substrate shown in FIG. 1.

FIG. 4 is a plan view of a cell culture kit shown in FIG. 1.

FIG. 5 is a bottom perspective view of a cell, culture kit shown in FIG. 1.

FIG. 6 is a cross-sectional view showing a state in which a cell culture kit is connected onto a substrate shown in FIG. 1.

FIG. 7 shows test results about whether fluid is precisely supplied at different flow rates through a micro-fluidic system for a perfusion cell culture according to the present disclosure.

FIG. 8a shows a test result about whether fluid is supplied in an accurate concentration distribution when the fluid is injected through a micro-fluidic system for a perfusion cell culture according to the present disclosure.

FIG. 8b is a graph showing a result of, a quantitative analysis of fluids in each well plate according to the test of FIG. 8a.

FIG. 9a shows a state in which culture media and drugs are injected accurately into well plates respectively in different concentration distributions.

FIG. 9b is a graph showing a measurement result of an amount of DNA extracted from each culture in each well plate as shown FIG. 9a using PI standing.

FIG. 9c is a graph showing a result of quantitative analysis of proteins contained in cells based on a concentration of each drug supplied into each well plate.

FIG. 10 is a diagram illustrating a mixing channel according to the present disclosure.

FIG. 11 is a graph showing a mixing efficiency based on a meandering characteristic of a mixing channel according to the present disclosure.

FIG. 12 is a photograph showing quantitatively injecting the fluid using a syringe pump (Harvard PHD 2000) in accordance with Example 2 of the present disclosure.

FIG. 13 is a photograph showing a result of a fluorescence analysis for Example 2.

FIG. 14 is a photograph of a standard sample prepared for producing a calibration curve for Example 2.

FIG. 15 is a graph showing luminous intensity data from fluorescence analysis of a standard sample for Example 2, where a calibration curve of a quadratic curve has an approximation value $R^2=0.9977$.

FIG. 16a shows a result of fluorescence analysis for Example 2, and

FIG. 16b shows a result of fitting a calibration curve for a concentration ratio.

FIG. 17 shows a result of fitting a calibration curve for a concentration ratio in case of a system without a bubble trap.

FIG. 18 is a photograph showing that when a bubble trap is included in a system of the present disclosure, bubbles injected into the system together with injected fluid thereto after a replacement of a syringe are captured in the bubble trap.

FIG. 19 and FIG. 20 show a system in accordance with Example 2 of the present disclosure containing a mixing channel.

DETAILED DESCRIPTION

Hereinafter, a micro-fluidic system according to an embodiment of the present disclosure will now be described in detail with reference to the accompanying drawings. Since various modifications may be applied to the present invention and the present invention may have several embodiments, particular embodiments will be illustrated in the drawings and described. However, it will be understood that the description herein is not intended to limit the claims to the specific embodiments described, on the contrary, it is intended to cover alternatives, modifications, and equivalents as may be included within the spirit and scope of the present disclosure as defined, by the appended claims. The same or similar reference numerals are used throughout the drawings and the description in order to refer to the same or similar constituent elements. In the accompanying drawings, the dimensions of the structure show an enlarged scale than actual for clarity of the disclosure.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

The terminology used herein is for the purpose of describing particular embodiments only and is not intended to be limiting of the present invention. As used herein, the singular forms "a," "an," and "the" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is an exploded perspective view showing a structure of a micro-fluidic system for a perfusion cell culture of the present disclosure. FIG. 2 is a plan view of an upper plate of a substrate shown in FIG. 1. FIG. 3 is a bottom perspective view of an upper plate of a substrate shown in FIG. 1. FIG. 4 is a plan view of a cell culture kit shown in FIG. 1. FIG. 5 is a bottom perspective view of a cell culture kit shown in FIG. 1.

Referring to FIG. 1 to FIG. 5, a micro-fluidic system for a perfusion cell culture according to an embodiment of the present disclosure includes a substrate 100, a micro-fluid injection channel 210, micro-fluid branch channels 220, micro-fluid outlet channels 230 and well plates 310.

The substrate 100 is a fluid supply plate having the micro-fluid injection channel 210, the micro-fluid branch channels 220, and the micro-fluid outlet channels 230 defined therein to supply a nutrient required for a cell culture to the well plates 310. The substrate 100 has a predetermined thickness to define therein the micro-fluid injection channel 210, the micro-fluid branch channels 220, and the micro-fluid outlet channels 230. For example, the substrate 100 may include an upper plate 100a and a lower plate 100b, each having a rectangular plate shape having a predetermined length. In this case, the micro-fluid injection channel 210, the micro-fluid branch channels 220, and the micro-fluid outlet channels 230 may be defined in the upper plate 100a or the lower plate 100b, and preferably, may be defined in the upper plate 100a with contacting a bottom face of the upper plate in order to facilitate supplying the fluid to the well plates 310. The upper plate 100a and the lower plate 100b may be superimposed and integrated with each other. In another example, the substrate 100 is monolithic, and the channels may be defined inside the single substrate.

The micro-fluid injection channel 210 is configured to guide the fluid injected into the substrate 100 along the plane direction of the substrate 100. For example, the micro-fluid injection channel 210 may be defend in the upper plate 100a on the bottom face thereof so as to guide the fluid in a direction of a long side of the rectangular plate shape.

The micro-fluid branch channels 220 divide the fluid flowing through the micro-fluid injection channel 210 toward the micro-fluid outlet channels 230 at a predetermined flow rate. To this end, the micro-fluid branch channels 220 may include two or more channels branched from the micro-fluid injection channel 210. In this connection, each micro-fluid branch channel 220 extends from the micro-fluid injection channel 210 to the micro-fluid outlet channel 230.

These micro-fluid branch channels 220 may have different lengths so that the flow rates of each branch channel may be different from each other based on the Poiseuille's law. The Poiseuille's law is expressed by Equation 1 as described above.

Based on the Poiseuille's law, the fluids flow at the different flow rates depending on the different lengths of the micro channels. That is, the fluid flowing through the micro-fluid injection channel 210 is divided and flowed into the micro-fluid branch channels 220. In this connection, divided flows into the micro-fluid branch channel 220 have different flow rates due to the different lengths thereof.

The micro-fluid branch channels 220 are designed based on the Poiseuille's law. Thus, the lengths of the micro-fluid branch channels 220 may be configured such that the flow rates change gradually, that is, increase or decrease gradually between the micro-fluid branch channels 220 arranged in the flow direction of the injected fluid from the injection channel.

For example, a number of the micro-fluid branch channels 220 may be four, and the lengths of the four micro-fluid branch channels 220 in the flow direction of the fluid may be respectively set to 69 mm, 40 mm, 21 mm, and 16 mm. In this case, the flow rates gradually decrease between the micro-fluid branch channels 220 arranged in the flow direction of the injected fluid from the injection channel. For example, the micro-fluid branch channels 220 having 69 mm, 40 mm, 21 mm, and 16 mm lengths respectively as arranged in the flow direction of the injected fluid from the injection channel may respectively have 40%, 30%, 20% and 10% flow rates.

The above design of the micro-fluid branch channels 220 facilitates comparative evaluation of nutrients supplies to individual well plate 310.

The micro-fluid outlet channels 230 discharge the fluid from the micro-fluid branch channels 220 toward the well plates 310 respectively. To this end, each of the micro-fluid outlet channels 230 extends from a distal end of each micro-fluid branch channel 220 toward a top face of the substrate 100 to define a through-opening through the top face of the substrate 100. These micro-fluid outlet channels 230 are arranged along the flow direction of the fluid.

Furthermore, the substrate 100 includes an inlet channel 110 and a cavity 120 for continuously supplying the fluid to the well plates 310 since the time when the fluid begins to be supplied into the substrate 100.

The inlet channel 110 is a channel used for injecting the fluid into the micro-fluid injection channel 210. In one example, the inlet channel 110 may include a fluid inlet 111 extending from a side face of the substrate 100 to an interior of the substrate 100 and an opening 112 communicating from an end of the fluid inlet 111 to the micro-fluid injection channel 210. The fluid inlet 111 may be located at a higher level than the micro-fluid injection channel 210, and may have an internal thread defined in an inner face thereof so that an adapter connected to a hose for supplying the fluid may be coupled to the fluid inlet 111 via the thread.

The cavity 120 defines a space for gathering the fluid discharged from the micro-fluid outlet channels 230. The number of he cavities 120 may be the same number as the number of the micro-fluid outlet channels 230, and each cavity 120 may be defined in the top face of the substrate 100 and may be located on each micro-fluid outlet channel 230. In this connection, the longest width of the cavity 120 is smaller than the shortest width of a bottom face of the well plate 310. Thus, the bottom face of the well plate 310 and an inner side face of the cavity 120 defines a space while the well plate 310 is located on the cavity 120. Each through opening 230 defined in the micro-fluid outlet channel communicates with the space in the cavity 120. Accordingly, the fluid discharged from the micro-fluid outlet channels 230 may be stored in the cavities 120.

Each well plate 310 stores a to-be-cultured cell and receive the fluid necessary for the cell culture through the micro-fluid injection channel 210, the micro-fluid branch channels 220, and the micro-fluid outlet channels 230. For this purpose, the number of the well plates 310 may be the same number as the number of the micro-fluid outlet channels 230. The plates 310 may be located on the top face of the substrate 100 and fluid-communicatively connected to the respective micro-fluid outlet channels 230. FIG. 6 is a cross-sectional view showing a state in which a cell culture kit is connected onto a substrate shown in FIG. 1.

Each well plate 310 may have a bottom plate 311 constituting a bottom portion of the well plate 310, and a side wall 312 extending vertically from the bottom plate 311. Each well plate 310 may have an opening 312a defined in an upper end of the side wall 312 so that a culture in each well plate 310 may be discharged through the opening 312a. Further, each well plate 310 may have at least one opening 311a defined in the bottom plate 311. Said one or more openings 311a may be fluid-communicatively connected to each cavity 120 in the substrate 100 to allow the fluid in the cavity 120 to inflow into a corresponding well plate 310 through said one or more openings 311a.

In this connection, these well plates 310 may form a single cell culture kit 300. The cell culture kit 300 may, have a plurality of cells, defined therein for the cell culture. Some of the cells constituting the single cell culture kit 300 may be defined as the well plates 310 connected to the micro-fluid outlet channels 230 respectively, while the remaining cells may be defined as culture receiving cells 320 configured for receiving cultures discharged through the openings 312a defined in the upper ends of the side walls 312 of the well plates 310 respectively. Each culture receiving cell 320 may have a bottom plate 321 and a side wall 322 and have the same shape as a corresponding, well plate 310. For example, the number of the culture receiving cells 320 may be two. In this case, the bottom plate 321 of each culture receiving cell 320 may have a discharging hole 321a defined therein for discharging the received culture in the cell.

In this case, as shown in FIG. 1, the well plates 310 may be arranged to form one central row among a plurality of the cells of the cell culture kit 300. The culture receiving cells 320 may be arranged to form remaining rows. In this connection, the side wall 322 of each of the culture receiving cells may have an opening 322a which is defined by partially cutting the side wall from a top to a bottom of the side wall 322. The kit has a closed bottom in a region between the row of the culture receiving cells 320 and the row of the well plates 310. Further, the opening 312a defined in the side wall 312 of each of the well plates 310 may face a neighboring culture receiving cell 320. The discharging hole 322a defined in the side wall 322 of each of the culture receiving, cells 320 may face an adjacent well plate 310. Using this structure, the culture discharged from each well plate 310 may be inflowed into the neighboring culture receiving cell 320.

In this way, in accordance with the present disclosure, the nutrient and the oxygen necessary for the cell culture are supplied to the well plates 310 through the micro-fluid channels, and, thus, the cells are cultured in the well plates 310. Further, the cultures in the well plates 310 are discharged through the discharging holes in the upper ends of the well plates 310 respectively. Thus, the perfusion cell culturing system may be provided in which the fluid is continuously supplied to the micro channels and then is continuously discharged through the discharging holes.

In this connection, when a bubble contained in the fluid enters the micro channels during the supply of the fluid in this perfusion cell culturing system, a channel clogging may occur and also an unintentional flow-resistance may occur in the micro channels. Thus, it may be difficult to supply the fluid in an accurate concentration distribution. To prevent this, the substrate 100 includes a bubble trap 130.

The bubble trap 130 defines a space for receiving the bubble contained in the fluid injected through the inlet channel 110. The bubble trap 130 may be located at a position of a path of the micro-fluid injection channel 210. For example, the bubble trap 130 may be located in the end of the micro-fluid injection channel 210 connected to the inlet channel 110 such that the trap is disposed between the inlet channel 110 for injecting the micro-fluid and the micro-fluid injection channel 210. In this connection, the bubble trap 130 may be positioned at a higher level than the micro-fluid injection channel 210.

Due to this bubble trap 130, when gas (bubble) is contained in the fluid injected from the inlet channel 110 to the micro-fluid injection channel 210, the bubble (gas) reaches the bubble trap 130 and rises up and exits into the bubble trap 130, while the fluid moves into the micro-fluid injection channel 210.

According to another embodiment of the present disclosure, the micro-fluidic system for the perfusion cell culture includes a further micro-fluid injection channel 240, further micro-fluid branch channels 250, a further inlet channel 140 and a further bubble trap 150. In this connection, in the above-mentioned embodiment, the micro-fluid injection channel, micro-fluid branch channels, inlet channel and bubble trap may be referred to as a first micro-fluid injection channel, micro-fluid branch channels, inlet channel and bubble trap, while further micro-fluid injection channel 240, the further micro-fluid branch channels 250, further inlet channel 140 and further bubble trap 150 may be referred to as a second micro-fluid injection channel 240, second micro-fluid branch channels 250, inlet channel 140 and bubble trap 150.

The second micro-fluid injection channel 240 is configured to guide the fluid injected into the substrate 100 along the plane direction of the substrate 100 as the first micro-fluid injection channel 210 does. The second micro-fluid injection channel 240 may not be coplanar with the injection channel 210 in the substrate 100. Alternatively, when the second micro-fluid injection channel 240 is coplanar with the first injection channel 210 in the substrate 100, the second micro-fluid injection channel 240 and the injection channel 210 are arranged to interpose a line corresponding to the well plate row therebetween. The second micro-fluid injection channel 240 may be parallel to the first micro-fluid injection channel 210. Further, the second micro-fluid injection channel 240 may be defined in the upper plate 100a with contacting, a bottom face of the upper plate so as to guide the fluid in a direction of a long axis of the rectangular plate shape. In an example, the second micro-fluid injection channel 240 may guide the fluid in a direction opposite to the flow direction of the fluid flowing through the first micro-fluid injection channel 210.

The second micro-fluid branch channels 250 divide the fluid flowing from the second micro-fluid injection channel 240 at a predetermined flow rate toward the micro-fluid outlet channels 230 respectively. To this end, the second micro-fluid branch channels 250 may be two or more channels branched from the second micro-fluid injection channel 240. In this connection, each second micro-fluid branch channel 250 extends toward each of the micro-fluid outlet channels from the second micro-fluid injection channel 240. That is, distal ends of the second micro-fluid branch channels 250 joint with the distal ends of the first micro-fluid branch channels 220 respectively and are fluid-communicatively connected to the micro-fluid outlet channels 230 respectively.

These second micro-fluid branch channels 250 may have different lengths so that the flow rates thereof are different from each other based on the Poiseuille's law. Thus, the lengths of the second micro-fluid branch channels 250 may be configured such that the flow rates change gradually, that is, increase or decrease gradually between the second micro-fluid branch channels 250 arranged in the flow direction of the injected fluid from the injection channel. The configuration of the second micro-fluid branch channels 250 is the same as that of the first micro-fluid branch channels 220. Thus, a detailed description thereof will be omitted.

The second inlet channel 140 is a channel for injecting the fluid into the second micro-fluid injection channel 240. In one example, the second inlet channel 140 may include a second fluid inlet 141 extending from a side of the substrate 100 opposite to the inlet channel 110 side to the inside of the substrate 100, and a second opening 142 communicating from an end of the second fluid inlet 141 to the second micro-fluid injection channel 240. The configuration of the second fluid inlet 141 is the same as that of the fluid inlet 111. Thus, a detailed description thereof will be omitted.

The second bubble trap 150 defines a space for receiving bubbles contained in the fluid injected through the second inlet channel 140. The second bubble trap 150 may be located at a position of the path of the second micro-fluid injection channel 240. For example, the second bubble trap 150 may be located in the end of the second micro-fluid injection channel 240 connected to the second inlet channel 140 such that the trap is disposed between the second inlet channel 140 for injecting the micro-fluid and the second micro-fluid injection channel 240. In this connection, the second bubble trap 150 may be located at a higher level than the second micro-fluid injection channel 240.

When the gas (bubble) is contained in the fluid injected from the second inlet channel 140 to the second micro-fluid injection channel 240, the bubble gas reaches the second bubble trap 150 and then the gas escapes into the second bubble trap 150 while the fluid moves into the second micro-fluid injection channel 240.

Using the micro-fluidic system for the perfusion cell culture according to the present disclosure, the nutrient and the oxygen necessary for the cell culture may be provided accurately into the well plates at the different concentration levels. Further, it is possible to observe and quantitatively evaluate proliferation of the cells cultured by the flows of the fluids dispensed in the different concentration distributions.

FIG. 10, FIG. 19 and FIG. 20 illustrate the system of the present disclosure which further includes a mixing channel. FIG. 20 illustrates a combined state of FIG. 19. FIG. 10 is an enlarged view of the branch channel. The mixing channel 1010 extends from the merging point between the distal end of the first branch channel and the distal end of the second branch channel to the micro-fluid outlet channel. The mixing channel 1010 may be positioned at a same level as that of the first or second fluid injection channel and the first or second branch channel. The distal end of the mixing channel is connected to a start point of the outlet channel. The outlet channel extends in a thickness direction of the substrate to the top face of the substrate.

The mixing channel includes a meandering section. As shown in FIG. 10, the meandering section means a section having a serpentine shape and facilitates mixing between different fluids introduced from the first and second channels, thereby reducing a straight length between two ends of the mixing channel.

In the case of a straight shaped mixing channel, a channel with 120 mm length was designed. The mixing between the fluids was checked. As a result, as shown in FIG. 11, it was confirmed that the two fluids are uniformly mixed so that C.V (Coefficient of variation) is 5% or smaller around 120 mm point. However, there is a disadvantage in that the length of the channel becomes larger. However, in the case of the meandering mixing channel, due to the serpentine shape, mixing performance is further improved compared to the straight shaped mixing channel, it was confirmed that the two fluids are uniformly mixed so that C.V (Coefficient of variation) is 5% or smaller around 60 mm point. That is, in the case of the meandering mixing channel, only 60 mm straight length of the mixing channel may suffice.

Example 1

The system illustrated in FIG. 1 was manufactured to evaluate the system of the present disclosure. FIG. 7 shows test results about whether the fluids are precisely supplied at the different flow rates through the micro-fluidic system for the perfusion cell culture according to the present disclosure. A dye was used for the test of FIG. 7.

FIG. 7a shows a test result when a blue dye is injected through the first inlet channel 110. As shown in FIG. 7a, the flow rates of the fluids as divided and, discharged into cavities 120 through the micro-fluidic outlet channels 230 respectively gradually decrease between the branch channels arranged in the flow direction of the fluid.

FIG. 7b shows a case where a yellow dye is injected through the second inlet channel 140. As shown in FIG. 7b, the flow rates of the fluids as divided and discharged into the cavities 120 through the micro-fluid outlet channels 230 respectively gradually decreases between the branch channels arranged in the flow direction of the fluid.

FIG. 7c shows a case where the blue dye and the yellow dye are injected through the inlet channel 110 and the second inlet channel 140, respectively. As shown in FIG. 7c, the flow rates of the fluids as divided and discharged into the cavities 120 through the micro-fluid outlet channels 230 respectively gradually decreases between the first and second branch channels respectively arranged in the first flow direction in the first micro-fluid injection channel 210 and the second flow direction in the second micro-fluid injection channel 240, respectively.

FIG. 8a shows a test result about whether the fluid is supplied in the accurate concentration distribution when the fluid is injected through the micro-fluidic system for the perfusion cell culture according to the present disclosure. For the test of FIG. 8a, DI-water was injected into the inlet channel 110, and a mixed solution of Bromphenol blue as fluorescent substance and DI-water was injected into the second inlet channel 140.

As shown in FIG. 8a, concentration gradients of the fluids as supplied to the well plates respectively are remarkably different, thereby confirming that the fluids are supplied in the accurate concentration distributions.

FIG. 8b is a graph showing the result of quantitative analysis of the fluid in each well plate according to the test of FIG. 8a.

As shown in FIG. 8b, it was confirmed that the concentration distributions of the fluids in the well plates increased linearly.

It was confirmed from the tests that using the micro-fluidic system for the perfusion cell culture according to the present disclosure, the nutrient and the oxygen required for the cell culture may be supplied at the different flow rates and in the accurate concentration distributions.

Further, the micro-fluidic system for the perfusion cell culture according to the present disclosure may be effectively used for an 3D-based perfusion cell culture experiment. To this end, after sequentially injecting culture media and drug (hydrogen peroxide) to the system, cell death results were checked based on concentrations of the drug.

FIG. 9a shows a state in which the culture media and the drugs are injected accurately into the well plates respectively at different concentration distributions. FIG. 9b is a graph showing measurement results of an amount of DNA extracted from the cultures in the well plates shown FIG. 9a using PI standing. FIG. 9c is a graph showing, a result of quantitative analysis of proteins contained in the cells based on the concentrations of the drugs supplied into the well plates.

As shown in FIG. 9b, a larger amount of DNA was measured at an early stage when the drug was added at a high concentration.

Meanwhile, after extracting surviving cells in each well plate, BOA protein quantitation analysis for the cells was executed. As a result, as shown in FIG. 9c, it may be confirmed that the amounts of the proteins contained in the cells vary depending on the concentrations of the added drugs.

Example 2

The system of the present disclosure illustrated in FIG. 19 and FIG. 20 including two micro-fluid injection channels was provided. In order to quantitatively inject fluid at an injection flow rate into the injection channel, a syringe pump (Harvard PHD 2000) as shown in FIG. 12 was used. Two syringes, each having 10 ml capacity were used for a long-term injection. For an experiment, the syringe and the present system are connected using a silicone tube. Further, a pipette and a 96 well plate were prepared. The fluid discharged from each well-plate was collected at a predetermined time interval. Then, the collected fluid was subject to fluorescence analysis.

One syringe injected the DI-water into the first micro-fluid injection channel, while the other syringe injected a mixture between methanol containing fluorescent substance rhodamine 110 dissolved therein and DI water into the second micro-fluid injection channel. FIG. 13 is referenced. In order to facilitate an operation of pump and the concentration gradient function at the same time, the inside of the channel was filled with the DI-water. When the channel is not filled with the DI-water, the bubble trap has been filled with bubbles before the experiment. Thus, the concentration gradient control may be difficult. Therefore, after operating the syringe pump in while the trap has been filled with the DI-water, the concentration gradient of the rhodamine 110 and the function of the bubble trap were checked. The fluid was injected at a flow rate of 80 μl/min. 150 μl of each sample was extracted from each well plate every 30 minutes since the time when the pump starts to be operated and the rhodamine 110 beings to be injected. The extracted sample was transferred to the 96 well-plate. In this way, the fluorescence analysis on the sample taken from each well over time was executed.

The fluorescence analysis result for the samples is expressed as a luminous intensity. In this connection, it is difficult to determine the amount of the concentration of the samples only using this luminous intensity. Thus, in order to quantitatively evaluate the concentration of the rhodamine 110 based on the resulting luminous intensity, standard samples are prepared to perform the fluorescence analysis. The standard samples were prepared by dissolving the rhodamine 110 in the methanol to form a solution and mixing the solution with the DI-water. Seven standard samples were produced at concentration ratios from 0.1 to 10. This is illustrated in FIG. 14. These standard samples were analyzed using fluorescence to obtain data of the luminous intensity based on controlled concentrations [g/ml]. The data are illustrated in Table 1 below. The data were represented as a graph in which a calibration curve of a quadratic curve was obtained. In the curve, an approximate value of $R^2=0.9977$ was confirmed. This is provided in FIG. 15. In this way, the luminosity of an arbitrary sample was fitted to the calibration curve and then the concentration amount of the sample is checked.

TABLE 1

| Concentration ratio | Concentration (g/ml) | Intensity |
| --- | --- | --- |
| 0 | 0 | 10 |
| 0.1 | 0.00248 | 134 |
| 0.3 | 0.00744 | 386 |
| 0.6 | 0.01488 | 630. |
| 1.2 | 0.02976 | 1002 |
| 2.5 | 0.062 | 2243 |
| 5 | 0.124 | 3556 |
| 10 | 0.248 | 5968 |

The fluorescence analysis of the samples collected from the 96 well plate was carried out using a FLUOstar OPTIMA microplate reader. Considering that an excitation wavelength and an emission wavelength of the rhodamine 110 were 496 and 520 nm respectively, the excitation and emission wavelengths of the reader were set to 485 and 520 nm respectively. A gain value was set to 100 to enable a measurement of the luminous intensity of the rhodamine 110.

From a result of the fluorescence analysis, as shown in FIG. 16a, the result of fitting the calibration curve to the concentration ratio is shown in FIG. 16b. it was confirmed that during the perfusion for 6 hours, the concentration of the rhodamine 110 was linearly graded in each well in general, and the concentration grade was maintained over time. In the experiment setup, the DI-water was filled in the channel. Thus, the experiment may start in a bubble-free environment. However, when the injection is performed for a long time, a capacity of the syringe is reduced, and, hence, a syringe replacement is required. In this replacement process, a separation between the syringe, the pump, and the system is inevitable, which causes the bubble to enter the system. From a result of the experiment using the system not including the bubble trap, the bubble penetrated into the channel and acted as a flow resistance, which made it impossible to adjust the concentration gradient as shown in FIG. 17. On the other hand, it was confirmed that when the system including the bubble trap was employed, the bubble injected into the system together with the injected fluid thereto after the syringe replacement was trapped in the bubble trap as shown in FIG. 18. Further, as shown in FIG. 16b as the result of the previous experiment, it was confirmed that the concentration gradient system was maintained stably during the perfusion for a long time.

This micro-fluidic system for the perfusion cell culture according to the present disclosure enables observation of the various cell cultures and cell proliferations and quantitative evaluation of the cell proliferation. For example, a micro-environment inside a living body may be simulated to observe a tumor growth in the living body and evaluate the growth in a quantitative manner.

The descriptions of the disclosed embodiments are presented to enable one of ordinary skill in the art to make and use the invention. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

What is claimed is:

1. A micro-fluidic system for a perfusion cell culture, the system comprising:
   a substrate;
   a micro-fluid injection channel defined in the substrate to guide fluid along the substrate;
   at least two micro-fluid branch channels defined in the substrate, wherein the branch channels are branched from the micro-fluid injection channel;
   a plurality of micro-fluid outlet channels defined in the substrate, wherein each of the outlet channels extends from a distal end of a respective branch channel of the plurality of branch channels to a top face of the substrate, wherein each outlet channel has a through-hole defined in the top face portion of the substrate; and
   well plates disposed on the top face of the substrate, wherein each of the well plates fluid-communicates with each outlet channel,
   wherein the substrate has a plurality of cavities defined in a top face portion thereof,
   wherein each through-hole in each outlet channel communicates with each cavity,
   wherein each well plate has at least one bottom-hole, and
   wherein a longest width of each cavity is smaller than a shortest width of a bottom face of each well plate, wherein a space is defined between a bottom face of each well plate and an inner face of each cavity, wherein fluid discharged from each through-hole is stored in each cavity, and, then, the fluid from each cavity is inflowed to a respective well plate through a respective at least one bottom-hole.

2. The system according to claim 1, wherein lengths of the branch channels are different from each other so that the branch channels have different flow rates based on Poiseuille's law.

3. The system according to claim 2, wherein the micro-fluid branch channels are sequentially arranged in a flow direction of the fluid guided by the micro-fluid injection channel, wherein the lengths of the branch channels are configured such that the flow rates increase or decrease gradually between the micro-fluid branch channels.

4. The system according to claim 1, wherein the substrate has an inlet channel defined therein for injecting micro-fluid to the injection channel, wherein the substrate has a bubble trap defined therein between the inlet channel and the injection channel.

5. The system according to claim 1, wherein each well plate has a lateral opening defined in an upper end of a side wall thereof, wherein a culture is discharged from each well plate through a lateral opening thereof.

6. A micro-fluidic system for a perfusion cell culture, the system comprising:
   a substrate;
   a micro-fluid injection channel defined in the substrate to guide fluid along the substrate;
   at least two micro-fluid branch channels defined in the substrate, wherein the branch channels are branched from the micro-fluid injection channel;
   micro-fluid outlet channels defined in the substrate, wherein each of the outlet channels extends from a distal end of each branch channel to a top face of the substrate, wherein each outlet channel has each through-hole defined in the top face portion of the substrate; and
   well plates disposed on the top face of the substrate, wherein each of the well plates fluid-communicates with each outlet channel,
   wherein the well plates are arranged to form a single row, wherein the substrate has a further micro-fluid injection channel defined therein, wherein the single row is interposed between the micro-fluid injection channel and said further micro-fluid injection channel, wherein the micro-fluid injection channel is parallel to said further micro-fluid injection channel,
   wherein the substrate has at least two further micro-fluid branch channels defined therein, wherein the further micro-fluid branch channels are branched from said further micro-fluid injection channel, and
   wherein a distal end of each of the at least two micro-fluid branch channels joints with a distal end of a respective branch channel of the at least two further micro-fluid branch channels, wherein each of said further branch channels fluid-communicates with each micro-fluid outlet channel.

7. The system according to claim 6, wherein lengths of the further branch channels are different from each other so that the further branch channels have different flow rates based on Poiseuille's law.

8. The system according to claim 7, wherein the further micro-fluid branch channels are sequentially arranged in a flow direction of fluid discharged from the further injection channel, wherein the lengths of the further branch channels are configured such that the flow rates increase or decrease gradually between the further micro-fluid branch channels.

9. The system according to claim 6, wherein the substrate has a further inlet channel defined therein for injecting micro-fluid to the further injection channel, wherein the substrate has a further bubble trap defined therein between the further inlet channel and the further injection channel.

10. The system according to claim 6, wherein the substrate has mixing channels defined therein, wherein each mixing channel extends from a respective jointing point to a respective micro-fluid outlet channel.

11. The system according to claim 7, wherein each mixing channel includes a meandering section.

* * * * *